United States Patent [19]
Woodward

[11] Patent Number: 5,462,968
[45] Date of Patent: Oct. 31, 1995

[54] EP$_2$-RECEPTOR AGONISTS AS AGENTS FOR LOWERING INTRAOCULAR PRESSURE

[75] Inventor: David F. Woodward, El Toro, Calif.

[73] Assignee: Allergan, Inc., Irvine, Calif.

[21] Appl. No.: 183,682

[22] Filed: Jan. 19, 1994

[51] Int. Cl.$^6$ .................................................. A61K 31/19
[52] U.S. Cl. ....................... 514/568; 562/492; 560/53; 514/530
[58] Field of Search ....................... 562/492; 514/568, 514/530; 560/53

[56] References Cited

U.S. PATENT DOCUMENTS

| | | |
|---|---|---|
| 4,494,274 | 2/1985 | Chan et al. . |
| 4,599,353 | 7/1986 | Bito . |
| 5,034,413 | 7/1991 | Chan et al. . |

FOREIGN PATENT DOCUMENTS 0364417  4/1990  European Pat. Off. .

OTHER PUBLICATIONS

Weeldon et al., Br. J. Pharmacol. (1993), 108(4), 1051–4.
Niols et al., Br. J. Pharmacol., 102, 24P (1991).
Starr. M. S., "Further Studies on the Effect of Prostalgnadin on Intraocular Pressure in the Rabbit", *Exp. Eye Research*, 1971, 11, pp. 170–177.
Bito, L. Z., "Prostaglandins, Other Eicosanoids, and Their Derivatives as Potential Antiglaucoma Agents," *Applied Pharmacology in the Medical Treatment of Glaucomas* Drance, S. M. and Neufeld, A. H. eds., New York, Grune & Stratton, 1984, pp. 477–505.
Nilsson, et. al., "PGF$_{2\alpha}$ Increases Uveoscleral Outflow", *Invest. Ophthalmol. Vis. Sci.* (suppl), 284, 1987.
Siebold, et al., "Esterified prostaglandin shows 'potent' promise", *Prodrug* 5 3, 1989.
Bito, L. Z., "Prostaglandins, Old Concepts and New Perspectives", *Arch. Ophthalmol.* 105, 1036, 1987.
Coleman, R. A., et al., "Prostanoids and their Receptors", *Comprehensive Medicinal Chemistry*, vol. 3, pp. 643–714, 1990.
Woodward et al, "Identification of 19 (R) —OH Prostaglandin E$_2$ as a Selective Prostanoid EP$_2$-Receptor Agonist", *Prostaglandins*, pp. 371–383, 1993.
Nials et al, "AH13205, A Selective Prostanoid EP$_2$–receptor Agonist", *Cardiovascular Drug Reviews*, vol. 11, No. 2, pp. 165–179 (1993).

*Primary Examiner*—Johann Richter
*Assistant Examiner*—John Peabody
*Attorney, Agent, or Firm*—Robert J. Baran; Martin A. Voet; J. Mark Hoch

[57] ABSTRACT

The invention relates to (±) trans-2-[-4(1-hydroxyhexyl) phenyl]-5-oxocyclopentaneheptanoic acid, and ester and unsaturated derivatives thereof, prostaglandin derivatives. More particularly, the present invention concerns compounds of the formula I

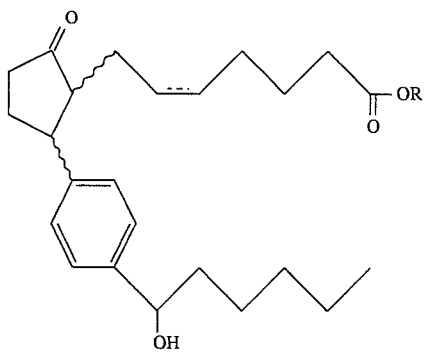

wherein the wavy bonds indicate that α or β configuration, the dashed bond represents either a single or double bond, which double bond may be a cis or trans double bond and R is a saturated or unsaturated acyclic hydrocarbon group having from 1 to about 20 carbon atoms, or —(CH$_2$)$_m$R$_1$ wherein m is 0–10, and R$_1$ is an aliphatic ring having from about 3 to about 7 carbon atoms, or an aryl or heteroaryl ring having from about 4 to about 10 carbon atoms and wherein the heteroatom is selected from the group consisting of N, O and S. The compounds of the present invention are potent ocular hypotensives, and are particularly suitable for the management of glaucoma.

3 Claims, No Drawings

EP$_2$-RECEPTOR AGONISTS AS AGENTS FOR LOWERING INTRAOCULAR PRESSURE

FIELD OF THE INVENTION

The present invention relates to the use of EP$_2$ receptor agonists to lower the intraocular pressure of mammals and thus are useful in treating glaucoma. In particular, (±) trans-2-[-4(1-hydroxyhexyl) phenyl]-5-oxocyclopentane-heptanoic-acid, and ester and unsaturated derivatives thereof, are effective for the management of glaucoma.

BACKGROUND OF THE INVENTION

Ocular hypotensive agents are useful in the treatment of a number of various ocular hypertensive conditions, such as postsurgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res*, 1971, 11, pp. 170–177; Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include PGF$_{2\alpha}$, PGF$_{1\alpha}$, PGE$_2$, and certain lipid-soluble esters, such as C$_1$ to C$_5$ alkyl esters, e.g. 1-isopropyl ester, of such compounds.

In the U.S. Pat. No. 4,599,353 certain prostaglandins, in particular PGE$_2$ and PGF$_{2\alpha}$ and the C$_1$ to C$_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest Ophthalmol. Vis. Sci.* 28(suppl), 284 (1987)].

The isopropyl ester of PGF$_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch, Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF$_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of United States patent applications assigned to Allergan, Inc. prostaglandin esters with increased ocular hypotensive activity accompanied with no or substantially reduced side-effects are disclosed. The U.S. Ser. No. 386, 835 (filed Jul. 27, 1989), relates to certain 11-acyl-prostaglandins, such as 11-pivaloyl, 11-acetyl, 11-isobutyryl, 11-valeryl, and 11-isovaleryl PGF$_{2\alpha}$. Intraocular pressure reducing 15-acyl prostaglandins are disclosed in the application U.S. Ser. No. 357,394 (filed May 25, 1989). Similarly, 11,15-9,15- and 9,11-diesters of prostaglandins, for example 11,15-dipivaloyl PGF$_{2\alpha}$ are known to have ocular hypotensive activity. See the patent applications U.S. Ser. No. 385,645 filed Jul. 27, 1990, now U.S. Pat. No. 4,494,274; 584,370 which is a continuation of U.S. Ser. No. 386,312, and 585,284, now U.S. Pat. No. 5,034,413 which is a continuation of U.S. Ser. No. 386,834, where the parent applications were filed on Jul. 27, 1989. The disclosures of these patent applications are hereby expressly incorporated by reference.

Finally, certain EP$_2$-receptor agonists are disclosed in Nials et al, *Cardiovascular Drug Reviews*, Vol. 11, No. 2, pp. 165–179, Coleman et al, *Comprehensive Medicinal Chemistry*, Vol. 3, pp. 643–714, 1990 and Woodward et al, *Prostaglandins*, pp. 371– 383, 1993.

SUMMARY OF THE INVENTION

We have found that certain EP$_2$-receptor agonists are potent ocular hypotensive agents. We have further found that (±) trans-2-[-4( 1-hydroxyhexyl) phenyl]-5-oxocyclopentaneheptanoicacid, and ester and unsaturated derivatives thereof, are especially useful in the treatment of glaucoma and surprisingly, cause no or significantly lower ocular surface hyperemia than the other compounds that are useful in lowering intraocular pressure, e.g. $PGF_{2\alpha}$ and lower alkyl esters thereof.

The present invention relates to methods of treating ocular hypertension which comprises administering an effective amount of a compound represented by the formula I

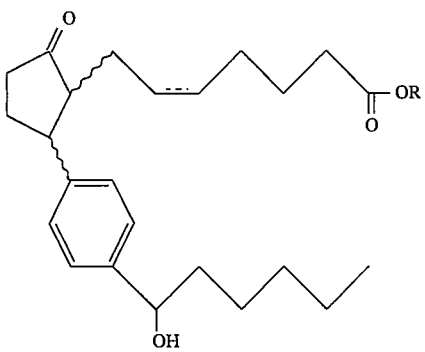

wherein, the wavy bands indicate the α or β configuration, R is a saturated or unsaturated acyclic hydrocarbon group having from 1 to about 20 carbon atoms, or $—(CH_2)_m R_1$ wherein m is 0–10, and $R_1$ is an aliphatic ring having from about 3 to about 7 carbon atoms, or an aryl or heteroaryl ring having from about 4 to about 10 carbon atoms, e.g. $R_1$ may be cyclohexyl, phenyl, thienyl, pyridyl or furanyl, or a pharmaceutically acceptable salt thereof and the dashed bond represents either a single or double bond which may be in the cis or trans position. Preferably $R_1$ is lower alkyl.

More preferably the method of the present invention comprises administering a compound represented by the formula II

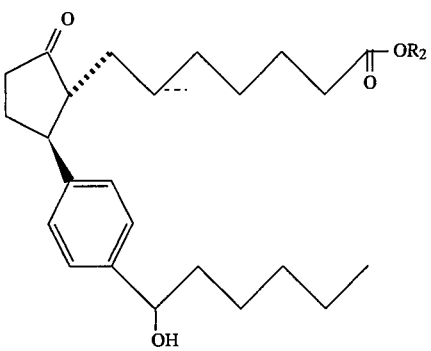

wherein $R_2$ is a lower alkyl radical and the other symbols are as defined above.

In a further aspect, the present invention relates to pharmaceutical compositions comprising a therapeutically effective amount of a compound of formulae (I) or (II) wherein the symbols have the above meanings, or a pharmaceutically acceptable salt thereof in admixture with a non-toxic, pharmaceutically acceptable liquid vehicle.

In a still further aspect, the present invention relates to certain (±) trans-2-[-4(1-hydroxyhexyl) phenyl]-5-oxocyclopentaneheptanoicacid, and ester and unsaturated derivatives thereof, of the above formulae, wherein the substituents and symbols are as defined hereinabove, or a pharmaceutically acceptable salt of such compounds.

DETAILED DESCRIPTION OF THE INVENTION

The present invention relates to the use of (±) trans-2-[-4(1-hydroxyhexyl) phenyl]-5-oxocyclopentaneheptanoic-acid, and ester and unsaturated derivatives thereof, as ocular hypotensives. These therapeutic agents are represented by compounds having the formula I

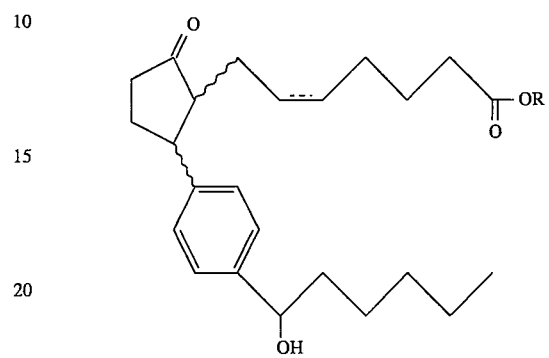

as defined above. The preferred compounds used in accordance with the present invention are encompassed by the following structural formula II

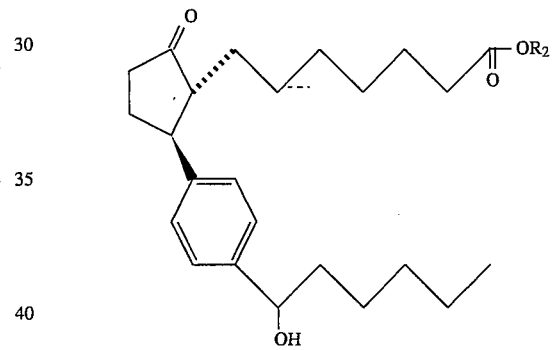

wherein $R_2$ is a lower alkyl radical.

In all of the above formulae, as well as in those provided hereinafter, the straight lines represent bonds. Where there is no symbol for the atoms between the bonds, the appropriate carbon-containing radical is to be inferred. For example in formula I, the radical between the cyclopentyl ring and the

radical is a polymethylene $(CH_2)$ radical, i.e. a hexylenyl radical. The dotted lines on the bond between carbons 5 and 6 (C-5), indicate a single or a double bond which can be in the cis or trans configuration. The radical adjacent the double bond is a CH radical. If two solid lines are used that indicates a specific configuration for that double bond. Hatched lines at positions C-9 and C-11 indicate the α configuration. If one were to draw the β configuration, a solid triangular line would be used.

In the compounds used in accordance with the present invention, compounds having the C-9 or C-11 substituents in the α or β configuration are contemplated. As hereinabove mentioned, in all formulas provided herein broken line attachments to the cyclopentane ring indicate substituents in the α configuration. Thickened solid line attachments to the cyclopentane ring indicate substituents in the β configuration.

For the purpose of this invention, unless further limited, the term "alkyl" refers to alkyl groups having from one to ten carbon atoms and includes "lower alkyl" radicals having from one to five carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of R may include a cyclic component, —$(CH_2)_m R_1$, wherein m is 0–10, $R_2$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_1$ preferably is phenyl, and the heteroaromatic rings have oxygen, nitrogen or sulfur as a heteroatom, i.e., $R_1$ may be thienyl, furanyl, pyridyl, etc. Preferably m is 0–4.

Preferred representatives of the compounds within the scope of the present invention are (±) trans-2-[-4(1-hydroxyhexyl)phenyl]-5-oxocyclopentaneheptanoicacid, unsaturated derivatives thereof, and lower alkyl esters of these compounds.

The following compound may be used in the pharmaceutical compositions and the methods of treatment of the present invention are (±) trans-2-[-4(1-hydroxyhexyl) phenyl]-5-oxocyclopentaneheptanoicacid.

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–8.0 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 µl.

The invention is further illustrated by the following non-limiting Examples.

EXAMPLE 1

(±) Trans-2-[-4(1-Hydroxyhexyl) Phenyl]-5-Oxocyclo- Pentaneheptanoicacid and Lower Alkyl Esters Thereof The above acid compound is well known and may be purchased or synthesized by methods known in the art. The lower alkyl esters of this compound may be made by the esterification procedures described in the various patent applications described in the Background of the Invention.

EXAMPLE 2

Intraocular Pressure

Intraocular pressure was measured by pneumatonometry in normal monkeys. Studies were performed in conscious animals trained to accept pneumatonometry. The compound of Example 1 was administered topically to one eye in a 25 µl volume drop, the contralateral eye received vehicle as a control. Statistical analysis was by Student's paired t test.

The intraocular pressure results are summarized in Table 1.

TABLE 1

EFFECT OF (±) TRANS-2-[-4(1-HYDROXYHEXYL) PHENYL]-5-OXOCYCLO PENTANE HEPTANOIC ACID, 0.1%, B.I.D. ON THE INTRAOCULAR PRESSURE OF NORMAL MONKEYS

| TIME (HR) RELATIVE TO FIRST DOSE | NET CHANGE IN PRESSURE (MMHg) |
|---|---|
| 0 | 0 |
| 2 | −1.17 |
| 4 | −2.0 |
| 6 | −1.50 |
| 24 | −0.67 |
| 26 | −1.0 |
| 28 | −1.83 |
| 30 | −1.50 |
| 48 | −1.50 |
| 50 | −2.33 |
| 52 | −1.50 |
| 54 | −1.50 |
| 72 | −2.33 |
| 74 | −2.17 |
| 76 | −2.33 |
| 78 | −2.0 |
| 96 | −1.83 |
| 98 | −2.0 |
| 100 | −2.0 |
| 102 | −2.0 |

(all changes in intraocular pressure are significant $p < 0.01$ according to Students t test)

EXAMPLE 3

Intraocular Pressure Reduction After Laser Treatment

Intraocular pressure reduction was also achieved in laser-induced ocular hypertensive monkeys. Ocular hypertension was induced by photocoagulating the trabecular meshwork by circumferential argon laser treatment.

TABLE 2

EFFECT OF A SINGLE DOSE (0.1%) OF TRANS-2-[-4(1-HYDROXYHEXYL)PHENYL]-5-OXO-CYCLOPENTANE-HEPTANOIC ACID ON OCULAR PRESSURE ON LASER-INDUCED OCULAR HYPERTENSIVE MONKEYS

| TIME (HR) RELATIVE TO FIRST DOSE | CHANGE IN INTRA-OCULAR PRESSURE (MMHg) |
|---|---|
| 0 | 0 |
| 1 | −4.5 |
| 2 | −6.0** |
| 4 | −4.7** |
| 6 | −4.5* |

*$p < 0.05$
**$p < 0.01$ (Students t test)

EXAMPLE 4

Determination of $EP_2$ Receptor Activity $EP_2$ receptor activity may be measured in accordance with the procedure disclosed in Woodward et al, *Prostaglandins*, pp. 371–383, 1993, which is hereby incorporated by reference in its entirety.

The foregoing description details specific methods and compositions that can be employed to practice the present invention, and represents the best mode contemplated. However, it is apparent from one of ordinary skill in the art that different pharmaceutical compositions may be prepared and used with substantially the same results. That is other $EP_2$-receptor agonists, such as $19R(OH)PGE_2$, butaprost, etc. will effectively lower intraocular pressure in animals and are within the broad scope of the present invention.

I claim:

1. A method of treating ocular hypertension which comprises applying to the eye an amount sufficient to treat ocular hypertension of a compound of formula I

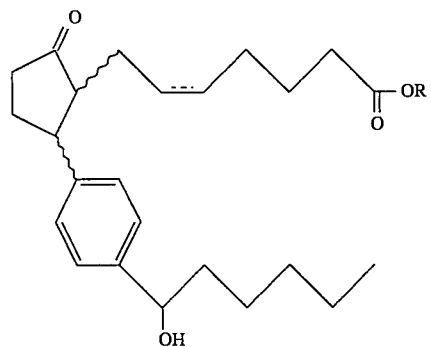

wherein the wavy bonds indicate that α or β configuration, the dashed bond represents either a single or double bond, which double bond may be a cis or trans double bond and R is hydrogen or a saturated or unsaturated acyclic hydrocarbon group having from 1 to about 20 carbon atoms, or $-(CH_2)_m R_1$ wherein m is 0–10, and $R_1$ is an aliphatic ring having from about 3 to about 7 carbon atoms, or phenyl.

2. The method of claim 1 wherein said compound is a prostaglandin derivative of the formula I

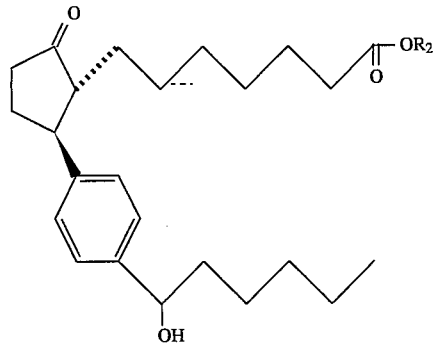

wherein $R_2$ is hydrogen or a lower alkyl radical, the hatched line indicates the α configuration and the solid triangular line indicates the β configuration.

3. The method of claim 2 wherein said compound is (±) trans-2-[-4(1 -hydroxyhexyl) phenyl]-5-oxocyclopentane-heptanoicacid.

* * * * *

UNITED STATES PATENT AND TRADEMARK OFFICE
CERTIFICATE OF CORRECTION

PATENT NO. : 5,462,968
DATED : October 31, 1995
INVENTOR(S) : David F. Woodward

It is certified that error appears in the above-indentified patent and that said Letters Patent is hereby corrected as shown below:

Column 6, line 64; delete "taneheptanoicacid" and insert in place thereof --taneheptanoic acid--

Column 7, line 62; delete "-4.5" and insert in place thereof -- -4.5** --

Column 8, line 65; delete "heptanoicacid" and insert in place thereof --heptanoic acid--

Signed and Sealed this

Fifth Day of March, 1996

Attest:

BRUCE LEHMAN

*Attesting Officer*  *Commissioner of Patents and Trademarks*